United States Patent
Kahlman et al.

(10) Patent No.: US 9,532,731 B2
(45) Date of Patent: Jan. 3, 2017

(54) METHOD AND APPARATUS FOR MEASURING THE CONCENTRATION OF A GAS IN EXHALED AIR

(75) Inventors: Josephus Arnoldus Henricus Maria Kahlman, Eindhoven (NL); Teunis Johannes Vink, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 740 days.

(21) Appl. No.: 13/500,922

(22) PCT Filed: Oct. 18, 2010

(86) PCT No.: PCT/IB2010/054701
§ 371 (c)(1),
(2), (4) Date: Apr. 9, 2012

(87) PCT Pub. No.: WO2011/048536
PCT Pub. Date: Apr. 28, 2011

(65) Prior Publication Data
US 2012/0203126 A1    Aug. 9, 2012

(30) Foreign Application Priority Data

Oct. 22, 2009    (EP) ..................................... 09173737

(51) Int. Cl.
*A61B 5/08* (2006.01)
*A61B 5/097* (2006.01)
*A61B 5/00* (2006.01)
*G01N 33/497* (2006.01)

(52) U.S. Cl.
CPC ............... *A61B 5/082* (2013.01); *A61B 5/097* (2013.01); *A61B 5/412* (2013.01); *G01N 33/497* (2013.01); *A61B 2562/028* (2013.01)

(58) Field of Classification Search
CPC ......... A61B 5/082; A61B 5/083; A61B 5/093; A61B 5/0935; A61B 5/097; A61B 5/08
USPC ................................ 600/529, 532, 538, 543
See application file for complete search history.

(56) References Cited

U.S. PATENT DOCUMENTS

| | | | |
|---|---|---|---|
| 6,038,913 A * | 3/2000 | Gustafsson et al. ........... 73/23.3 |
| 6,599,253 B1 * | 7/2003 | Baum et al. ................... 600/532 |
| 6,629,933 B1 * | 10/2003 | Lindner ........................ 600/532 |
| 7,156,813 B2 | 1/2007 | George et al. |
| 7,377,901 B2 * | 5/2008 | Djupesland et al. ......... 600/529 |
| 7,427,269 B2 | 9/2008 | George et al. |
| 2001/0029340 A1 | 10/2001 | Mault et al. |
| 2003/0050567 A1 | 3/2003 | Baghdassarian |
| 2003/0109795 A1 | 6/2003 | Webber |

(Continued)

FOREIGN PATENT DOCUMENTS

| | | |
|---|---|---|
| CN | 101354394 | 1/2009 |
| EP | 1792566 A2 | 6/2007 |

(Continued)

*Primary Examiner* — Christian Jang
(74) *Attorney, Agent, or Firm* — Michael W. Haas

(57) ABSTRACT

There is provided an apparatus for monitoring the respiration of a subject, the apparatus comprising a sensor for measuring the concentration of a specified gas in air exhaled by the subject and a processor configured to provide an output indicating the concentration of the specified gas in a selected portion of the exhaled air, the selected portion of the exhaled air corresponding to air from a specific part of the respiratory system of the subject.

16 Claims, 2 Drawing Sheets

(56) References Cited

U.S. PATENT DOCUMENTS

| | | |
|---|---|---|
| 2003/0208131 A1 | 11/2003 | George |
| 2004/0210154 A1* | 10/2004 | Kline |
| 2005/0159666 A1* | 7/2005 | Pearce et al. ................. 600/509 |
| 2005/0177056 A1* | 8/2005 | Giron et al. .................. 600/543 |
| 2006/0241507 A1* | 10/2006 | Carlson et al. ............... 600/532 |
| 2007/0048180 A1 | 3/2007 | Gabriel |
| 2007/0073183 A1* | 3/2007 | Kline ............................ 600/532 |
| 2007/0167853 A1* | 7/2007 | Melker et al. ................ 600/532 |
| 2007/0232950 A1* | 10/2007 | West ............................. 600/532 |
| 2008/0127977 A1 | 6/2008 | Orr |
| 2009/0054798 A1 | 2/2009 | Verney et al. |

FOREIGN PATENT DOCUMENTS

| | | | | |
|---|---|---|---|---|
| EP | 1792566 A3 | | 7/2007 | |
| EP | 1985993 A1 | | 10/2008 | |
| IL | WO-2010/001390 | * | 1/2010 | ............ A61B 5/087 |
| WO | WO2004000400 | | 12/2003 | |
| WO | WO -2009/001275 | * | 12/2008 | ............... A61B 5/08 |
| WO | WO-2009001275 | * | 12/2008 | ............... A61B 5/08 |
| WO | WO2009001275 | | 12/2008 | |
| WO | WO 2009001275 A1 | * | 12/2008 | |
| WO | WO -2010/001390 | * | 1/2010 | ............ A61B 5/087 |
| WO | WO 2010001390 A1 | * | 1/2010 | |

\* cited by examiner

METHOD AND APPARATUS FOR MEASURING THE CONCENTRATION OF A GAS IN EXHALED AIR

TECHNICAL FIELD OF THE INVENTION

The invention relates to the measurement of the concentration of a particular gas in a gaseous stream exhaled by a subject.

BACKGROUND TO THE INVENTION

Conditions such as asthma can be managed by measuring the concentration of nitric oxide (NO) in the air exhaled by a subject. Those suffering from asthma produce elevated levels of NO in the lower respiratory tract (the bronchi and alveolar part).

Currently, for a NO measurement to be performed, the patient must exhale at a constant air-flow rate of 50 ml/s for 10 seconds. Due to a flow restrictor, the pressure in the mouth cavity of the subject is high enough to close the velum—the soft palate consisting of muscle fibers sheathed in mucous membrane responsible for closing off the nasal passages during the act of swallowing and sneezing—thereby preventing NO from the nose from disturbing the measurement.

However, in this method, NO concentrations are extremely low, and a sensitive and expensive system is required to measure the parts-per-billion concentrations of NO in exhaled air and to integrate the measurements over time. Even so, the result is prone to errors and offset due to NO produced by glands in the upper airways of the subject.

Furthermore, the current detection techniques are based on the subject maintaining a near constant exhalation for a period of 10 seconds, which is not easy or even possible for older subjects, young children or subjects having difficulty breathing. The relatively large volume of exhaled gas is required in order to achieve a sufficient signal-to-noise ratio (SNR) in the NO measurement. Furthermore this method is not ideally applicable for use in continuous monitoring of subjects.

Furthermore, in the case where the NO concentration is measured during normal breathing (i.e. in continuous monitoring) the nose has to be blocked to avoid errors and offset due to residual NO production in the nasal glands. This blocking is very inconvenient for the subject.

Therefore, there is a need for an improved method and apparatus for measuring the concentration of nitric oxide (and other specific gases) in an exhaled gaseous stream.

SUMMARY OF THE INVENTION

Therefore, according to a first aspect of the invention there is provided an apparatus for monitoring the respiration of a subject, the apparatus comprising a sensor for measuring the concentration of a specified gas in air exhaled by the subject; and a processor configured to provide an output indicating the concentration of the specified gas in a selected portion of the exhaled air, the selected portion of the exhaled air corresponding to air from a specific part of the respiratory system of the subject.

According to a second aspect of the invention, there is provided a corresponding method of monitoring the respiration of a subject, the method comprising measuring the concentration of a specified gas in air exhaled by the subject; and providing an output indicating the concentration of the specified gas in a selected portion of the exhaled air, the selected portion of the exhaled air corresponding to air from a specific part of the respiratory system of the subject.

BRIEF DESCRIPTION OF THE DRAWINGS

The invention will now be described, by way of example only, with reference to the following drawings, in which.

DETAILED DESCRIPTION OF THE PREFERRED EMBODIMENTS

Figure 1:
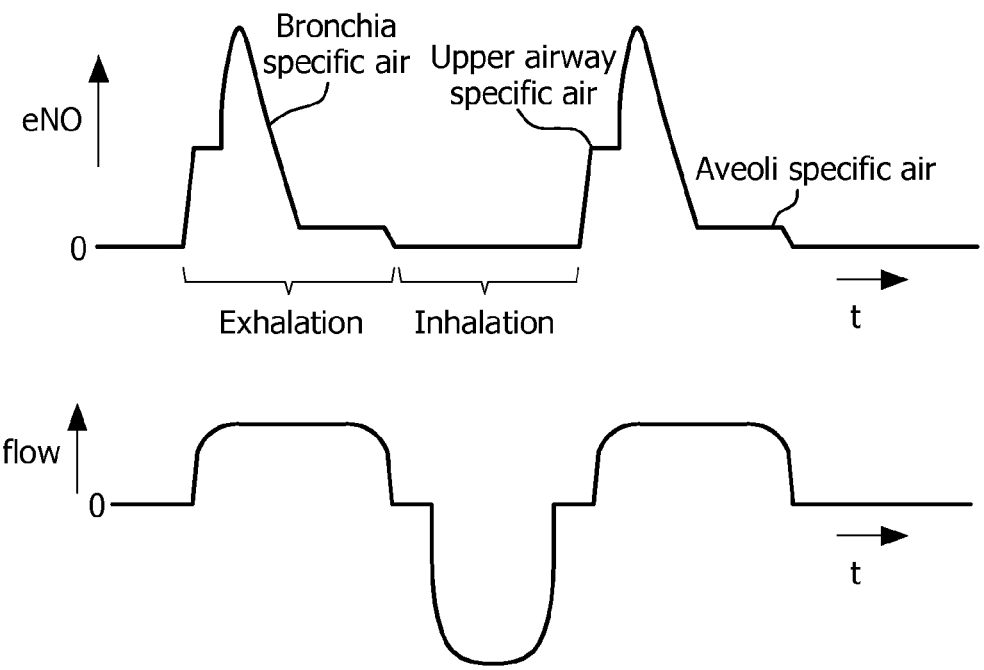
FIG. 1 illustrates a concentration profile for nitric oxide in an exhaled gaseous stream (top graph) and air flow (bottom graph) during normal breathing of a subject with asthma.

Although the invention will be described below with reference to the detection of nitric oxide (NO) in gas exhaled by a subject, it will be appreciated that the invention can be applied to the detection of other specific gases in an exhaled gaseous stream.

In particular, the analysis of exhaled breath is an important monitoring tool in modern medicine. Through the analysis of the fluid mechanical properties such as flow and volume, information about pulmonary functions can be extracted. For example, as the lungs are the location where the gases are exchanged between blood and air, the difference of major air constituents such as oxygen, carbon dioxide and water vapor between inhaled and exhaled air are indicative of the levels of arterial blood gases. In addition, the diffusion of anaesthetic agents can be followed through breath analysis. Finally, trace markers such as nitric oxide can provide information on pathologies in the respiratory system.

Carbon dioxide is exchanged between the air and the blood in the lungs through its dense perfusion and pulmonary aveoli (also known as alveoli) which offer a maximal exchange surface. As the carbon dioxide diffuses from the blood to the air to reach a certain diffusion equilibrium, the level of carbon dioxide in the exhaled air is strongly related to the pressure of carbon dioxide in the blood ($pCO_2$). In particular, at the end of the exhalation, the air from near to the aveoli is expelled from the lungs. As there is equilibrium in the levels of carbon dioxide in the blood and the exhaled air, the end tidal carbon dioxide value ($EtCO_2$) is the $pCO_2$ value in the blood (within a 5% error range). This value is important as it quantifies the metabolism of a person. It is monitored continuously for any person having assisted breathing.

It is known that various medical conditions cause changes in the level of nitric oxide produced in a subject, and in the level of nitric oxide produced by particular parts of the respiratory system of the subject. For example, subjects suffering from asthma produce elevated levels of nitric oxide in the lower respiratory tract part of the respiratory system (the bronchi), whereas pneumonia leads to a rise in the nitric oxide produced in the lower part of the respiratory system (the aveoli).

As the current techniques for measuring NO levels have a limited volume specificity, they are unable to follow the dynamics of the NO concentration profile in the exhaled gaseous stream or to correspond the outcome to a specific part of the respiratory system.

Thus, the present invention is based on the recognition that the maximum NO concentration produced in a specific part of the respiratory system is present in an air-volume that has been in that part of the respiratory system for the longest length of time. Thus, in subjects suffering from asthma, the maximum NO concentration will be obtained from the volume of exhaled gas that was present in the bronchia for the longest period of time.

It will be appreciated that in the ideal situation, when air stands still in the bronchia, the maximum amount of NO molecules are absorbed into that air. This means that integration over time takes place in the bronchia themselves, so that the local concentration of NO is much higher than in the air in other parts of the respiratory system such as the aveoli or upper airways. If this part of the total exhaled volume can be selected and sampled, then the detection of the concentration of nitric oxide can be significantly improved.

This can be further illustrated with reference to FIG. 1 which shows a concentration profile of nitric oxide in an exhaled gaseous stream (top graph) and air flow (bottom graph) during normal breathing of a subject with asthma.

During inhalation, nitric oxide from the surrounding environment enters the respiratory system. On the way towards the aveoli, the inhaled air collects additional nitric oxide molecules produced in the upper airways (for example the nose) and the bronchia. In the aveolar area almost all nitric oxide molecules are dissolved into the blood, hence the exhaled nitric oxide (eNO) level in air (measured in parts per billion, ppb) from the aveoli has a very low value.

During exhalation by an asthmatic subject, in a first order approximation, the exhaled air can be divided into three portions. The first portion of the exhaled air corresponds to the air from the upper airway (for example the trachea), and has a particular eNO level (determined by the NO produced in the nose and by the level of NO in the environment). The second portion of the exhaled air corresponds to the air from the bronchia (which is around 150 ml in volume) and has an eNO level that is significantly higher than that in the air from the upper airway. The third portion of the exhaled air corresponds to the air from the aveoli that is substantially NO-free (as the NO has been absorbed into the blood) and that collects NO while passing through the bronchia and upper airways. It is this portion of the exhaled air that makes up the majority of the air used in the prior art measurement techniques.

It will be appreciated that the concentration profile shown in FIG. 1 has been exaggerated in order to illustrate the principles underlying the invention, and that an actual concentration profile will not have such sharp or defined maxima and minima since the exhaled volume of air passes a number of locations where NO is produced or absorbed.

Figure 2:
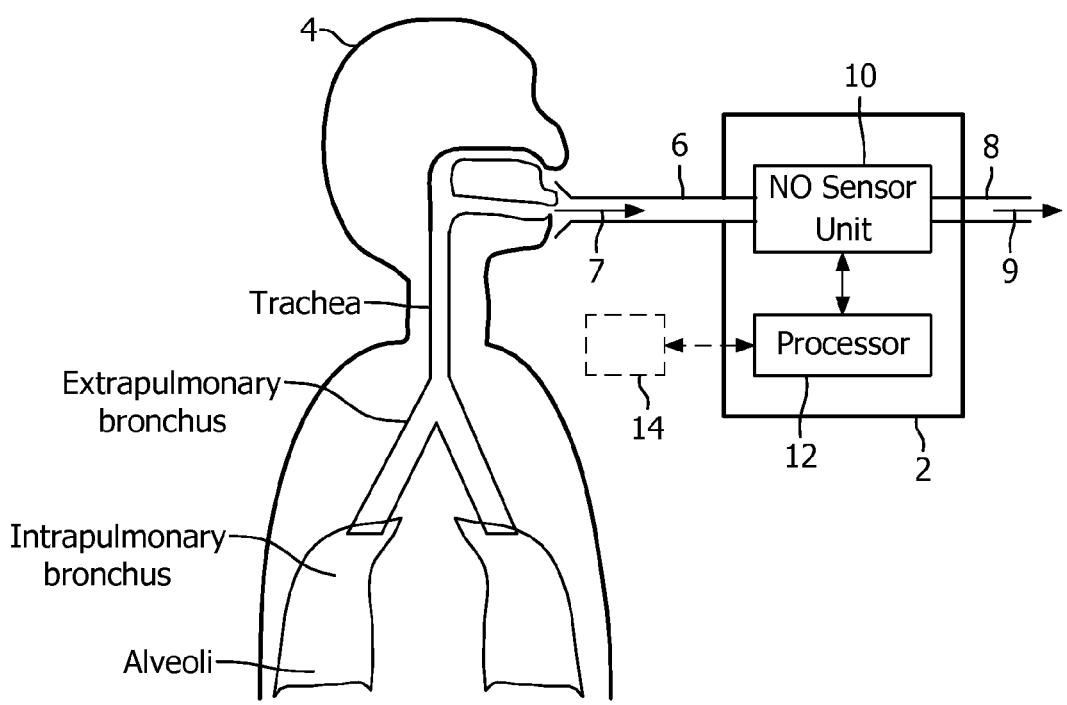
FIG. 2 is an illustration of an apparatus according to the invention being used by a subject.

Thus, a method and an apparatus has been developed that provide improvements in the measurement of NO levels in exhaled air. An illustration of an apparatus 2 in accordance with the invention is shown in FIG. 2. An outline of the main parts of the respiratory system of the subject 4 are also shown in FIG. 2, and in particular the upper airways, the bronchia and the aveoli.

The apparatus 2 comprises an air inlet 6 that the subject 4 exhales into (as indicated by arrow 7), an air outlet 8 by which the exhaled air exits the apparatus 2 (as indicated by arrow 9), a NO sensor unit 10 disposed between the air inlet 6 and air outlet 8 for analyzing the NO level or concentration in the exhaled air, and a processor 12 that is coupled to the NO sensor unit 10 for controlling the NO sensor unit 10 and for processing the NO measurements.

The air inlet 6 may comprise a simple tube into which the subject 4 can exhale, or a breathing mask or similar arrangement that can be worn by the subject 4 while they are being monitored. It will be appreciated by those skilled in the art that the air inlet 6 may also include means for allowing the subject 4 to inhale air without having to draw air through the main part of the apparatus 2 itself. For example, the air inlet 6 may have a first one-way valve for allowing exhaled air to be passed to the NO sensor 10 in the direction of arrow 7 and a second one-way valve for allowing the subject 4 to draw air into the air inlet of the subject 4 from the surrounding environment when they inhale.

The NO sensor unit 10 is configured so that it can regularly sample small amounts of the exhaled air to build up a profile of the NO concentration level in the exhaled air. In a preferred embodiment, each sample comprises 20 ml or less of exhaled air, as this sample size brings out the variation of the NO concentration level in the exhaled air. In particular, because the response of the NO sensor unit 10 is given by the convolution of the sample volume and the exhaled air, the sample volume must be small enough not to affect the NO concentration profile. NO sensors are known in the art, and will not be described further herein.

In one embodiment, microelectromechanical systems (MEMS) devices can be used to capture and sample the exhaled air, which allows sub-milliliter resolution to be achieved. Such sensors can comprise a relatively slow responding chemical sensor device having a (MEMS) sampling unit.

Figure 3:
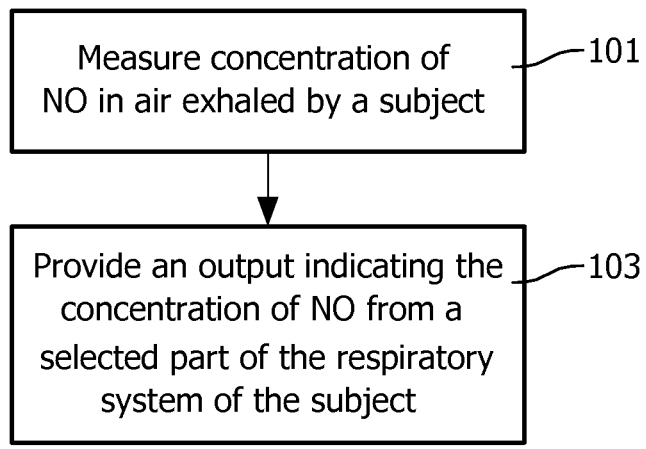
FIG. 3 is a flow chart illustrating a general method in accordance with the invention.

FIG. 3 illustrates a general method in accordance with the invention that is performed by the apparatus 2. In step 101, the concentration of NO in air exhaled by the subject 4 is measured by the NO sensor unit 10. Then, in step 103, an output is generated by the processor 12 that indicates the concentration of NO from a selected portion of the exhaled air, the selected portion corresponding to air from a specific part of the respiratory system of the subject 4.

The general method according to the invention can be implemented in two main ways by the apparatus 2. In a first implementation, the concentration of NO in exhaled air is sampled during a full exhalation by the subject 4, and a subset of the samples are identified that correspond to the measurements of the NO in air from the required part of the respiratory system of the subject 4. In a second implementation, the concentration of NO in exhaled air is sampled only during a selected part of the full exhalation by the subject 4.

In these implementations, it is necessary for the apparatus 2 to determine which part of the exhalation should provide the samples that form the basis of the output. Thus, in the first implementation, it is necessary for the processor 12 to determine, from the samples covering the complete exhalation, which samples cover the selected part of the exhalation. In the second implementation, it is necessary for the processor 12 to identify the selected part of the exhalation and to activate the NO sensor unit 10 to sample the NO concentration during this part.

In the first implementation, the processor 12 may be able to determine which samples cover the selected part of the exhalation by examining the NO concentration profile. For example, if the subject 4 is suffering from asthma, the processor 12 will be able to examine the NO concentration profile and extract the samples of the air from the bronchia as the samples that produce the maximum values for the NO concentration.

In an embodiment (applicable to both implementations), the apparatus 2 can include at least one further sensor 14 (illustrated with a dashed line in FIG. 2) for providing the processor 12 with an indication of the timing of the breathing of the subject 4. Using this indication of the timing, the processor 12 can select the appropriate samples or activate the NO sensor unit 10 at the appropriate time to provide the required output.

In particular, the processor 12 can use the indication of the timing with an identified peak in the sample values to identify samples for a particular part of the breathing cycle (whether or not that part corresponds to the peak). For example, if it was desired to determine the level of NO (or another gas) from the upper airways in a patient with asthma, the processor 12 could identify the peak from the NO sample values and use the indication of the timing and periodicity of the breathing cycle from the sensor 14 to select the samples corresponding to air exhaled from the upper airways (i.e. samples that occur before the peak in the NO sample values).

Alternatively, where the processor 12 activates the NO sensor unit 10 to collect samples at the appropriate times, the processor 12 can use the indication of the timing of the breathing cycle to identify the correct part of the exhalation to be sampled by the NO sensor unit 10.

The at least one further sensor 14 can include one or more of the following sensor types: (i) an airflow sensor that is incorporated into the air inlet 6 or NO sensor unit 10 for detecting when the subject 4 starts and stops exhaling; (ii) a movement sensor (such as an accelerometer) that is attached to the chest of the subject 4 to monitor the orientation and/or rise and fall of the chest of the subject 4; and (iii) a microphone that is placed near to the subject's throat to monitor the sound of the subject's breathing.

Those skilled in the art will be aware of many other types of sensor that can be used for providing the processor 12 with an indication of the timing of the breathing of the subject 4.

It will also be appreciated that if the subject 4 is being artificially ventilated, an indication of the breathing rhythm can be provided to the processor 12 from the ventilator.

The processor 12 may implement an adaptive technique to identify the proper sample timing or the required volume of exhaled air to be sampled by making use of samples in measurements of subsequent exhalations of the subject 4.

In particular, the processor 12 can maximize the outcome of the NO measurement by identifying a region of interest in the samples where the NO concentration reaches its maximum (for example the peaks in the top graph of FIG. 1). The processor 12 can then adjust the time interval in which the exhaled air is sampled based on the maximized eNO level.

Alternatively, synchronized with the breathing of the subject, the timing of the selected samples can be varied across the breathing curve in order to measure the eNO at each time (or part of) the breathing cycle. The sample-time is short enough to follow the dynamics of the time varying eNO. The signal to noise ratio can be enhanced by combining (averaging) samples taken at the same positions during subsequent breathing cycles. The processor 12 can then select the eNO measurement for the appropriate part of the exhalation of the subject 4 from the averaged samples.

The part of the exhalation to be "selected" will be determined by the purpose to which the apparatus 2 is to be put. For example, if the apparatus 2 is to be used to monitor subjects 4 with asthma, then in either implementation above the apparatus 2 can be configured to output the NO concentration level obtained from the samples of the exhaled air that came from the bronchia of the subject 4. Alternatively, the apparatus 2 can be capable of monitoring a number of different medical conditions that cause altered NO levels in different parts of the respiratory system of a subject 4, which means that a healthcare professional can configure the apparatus 2 to output the NO concentration level for samples of the exhaled air from the required part of the respiratory system of the subject 4.

In one embodiment, the signal-to-noise ratio of the output NO concentration level can be improved by performing the measurements on subsequent exhalations by the subject 4 and averaging the results.

It will be appreciated that it is possible to compensate for environmental NO concentration levels in air from the upper airway of the subject 4 by sampling the NO concentration level in air as it is being inhaled by the subject 4.

It will be appreciated from the above that the apparatus 2 according to the invention can be used to measure NO concentration levels during normal breathing by the subject 4 (i.e. the 10 second exhale of the prior art techniques is no longer required), which is particularly useful if the apparatus 2 is to be used to continuously monitor the breathing of a subject 4.

As described above, the apparatus 2 can be applied to several different medical conditions. Asthma has been discussed extensively above, but the apparatus 2 can be used to monitor subjects for lower airway (aveoli) infections such as pneumonia, or the start of upper airway infections and sepsis in pre- and post-operative patients in an intensive care unit or general ward of a hospital.

Figure 4:
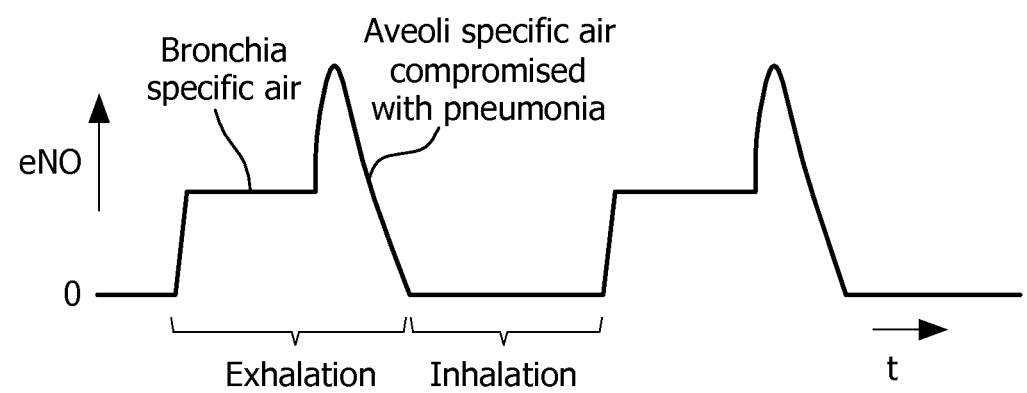
FIG. 4 illustrates a concentration profile for nitric oxide in an exhaled gaseous stream (top graph) and air flow (bottom graph) during normal breathing of a subject with pneumonia.
Figure 4:
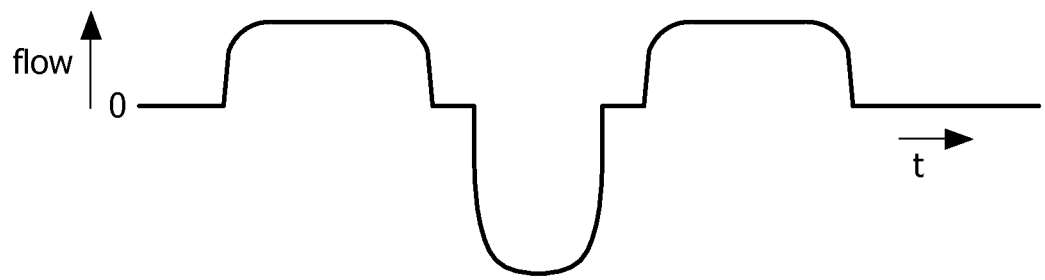

FIG. 4 illustrates a concentration profile for nitric oxide in an exhaled gaseous stream (top graph) and air flow (bottom graph) during normal breathing of a subject with pneumonia. Thus, it can be seen that the NO concentration level for the air from the aveoli is much higher than the air from the bronchia or upper airway.

Further improvements in the NO concentration measurements made by the apparatus 2 can be obtained if the subject 4 holds their breath for a short period before exhaling. This is normally much easier for subjects than maintaining a constant exhalation flow for around 10 seconds. During the time that the subject 4 holds their breath, the NO produced in the bronchia integrates into the air, which means that the concentration of the NO in the exhaled air will be higher (improving the signal to noise ratio).

This also allows the apparatus 2 to operate without requiring the further sensor 14. The NO concentration level can be measured by the apparatus 2 as a function of time, and a specific time interval in the measurements corresponding to a peak in the NO concentration level can be selected by the processor 12 to provide the NO measurement for the air from the selected part of the respiratory system of the subject 4. If the selected part is the bronchia, the background NO concentration level from the nose, throat (trachea) and environment can be removed by correlating the NO concentration profile with the NO concentration during regular inhalation and exhalation.

In a further variation, a part of the exhaled air is first sampled and then measured, with the selected time interval being adaptively optimized by maximizing the outcome of the NO measurement.

There is therefore provided an improved method and apparatus for measuring the concentration of nitric oxide (and other specific gases) in an exhaled gaseous stream.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An apparatus for monitoring the respiration of a subject, the apparatus comprising:
   a gas concentration sensor configured to measure a concentration of a specified gas in exhaled air by the subject; and
   a physical computer processor in communication with the sensor configured by machine-readable instructions such that the apparatus for monitoring the respiration electronically determines the concentration of the specified gas in the exhaled air at least by measuring the concentration of the specified gas in air exhaled from bronchia of the subject as distinct from gas from alveoli of the subject, the machine-readable instructions causing the physical computer processor to:
   identify portions of the exhaled air that corresponds to air exhaled from an upper airway, the alveoli, and the bronchia of a respiratory tract of the subject;
   activate the sensor, in response to identifying a portion of the exhaled air from the bronchia, to measure the concentration of the specified gas in the exhaled air from the bronchia; and
   provide an output indicating the concentration of the specified gas in the exhaled air from the bronchia of the subject.

2. The apparatus as claimed in claim 1, wherein the sensor is configured to obtain samples of the specified gas in the exhaled air from the bronchia, and wherein the processor is configured to provide the output by selecting an appropriate one or ones of the samples that correspond to measurement of the air from the bronchia based on a timing of the samples taken during exhalation.

3. The apparatus as claimed in claim 2, wherein the processor is configured to examine the samples of the specified gas in the exhaled air from the bronchia to identify a peak or peaks in the samples of the concentration of the specified gas and to select an appropriate one or ones of the samples as those samples that represent the bronchia of the subject based on the timing of the peak or peaks in the concentration of the specified gas.

4. The apparatus as claimed in claim 1 further comprising a time sensor configured to provide an indication of the timing of the exhalation of the subject; wherein the processor is configured to use the indication of the timing to identify the exhaled air from the bronchia.

5. The apparatus as claimed in claim 4, wherein the processor is further configured to use the indication of the timing to activate the sensor to obtain samples of the specified gas during exhalation of air from the bronchia, the alveoli, and the upper airway, and to provide the output for the bronchia, the alveoli, and the upper airway from the samples.

6. The apparatus as claimed in claim 1, wherein the processor is configured to determine the concentration of the specified gas in the exhaled air from the bronchia over a plurality of exhalations, and to provide the output as an average of the concentration of the specified gas over the plurality of exhalations.

7. The apparatus as claimed in claim 1, wherein the sensor is further configured to measure a concentration of the specified gas in air inhaled by the subject, and the processor is configured to obtain a level of the specified gas in the environment from the air inhaled by the subject and subtract the measurement of the concentration of the specified gas in the inhaled air from measurements of the concentration of the specified gas in the exhaled air from the bronchia.

8. The apparatus as claimed in claim 1, wherein the sensor is configured to measure the concentration of the specified gas at regular intervals during exhalation of air from the bronchia.

9. The apparatus as claimed in claim 8, wherein the sensor is configured to measure the concentration of the specified gas in volumes of 20 ml or less of the exhaled air from the bronchia.

10. The apparatus as claimed in claim 1, wherein the sensor is configured to measure the concentration of nitric oxide, NO.

11. The apparatus as claimed in claim 1, wherein the apparatus is configured for use in monitoring subjects for asthma.

12. The apparatus as claimed in claim 1, wherein the exhaled air from the bronchia includes dead-space air measured to diagnose asthma.

13. A method of monitoring respiration of a subject with a monitoring system, the monitoring system comprising a user interface, a sensor, and a physical computer processor, the method electronically determining a concentration of a specified gas in exhaled air at least by measuring the concentration of the specified gas in air exhaled from bronchia of the subject as distinct from gas from alveoli of the subject, the method comprising:
   identifying, with the physical computer processor, a-portions of the exhaled air that corresponds to air exhaled from an upper airway, the alveoli, and the bronchia of a respiratory tract of the subject;
   activating, in response to identifying a portion of the exhaled air from the bronchia with the physical computer processor, the sensor to measure a concentration of the specified gas in the exhaled air from the bronchia; and
   providing, with the physical computer processor, an output indicating the concentration of the specified gas in the exhaled air from the bronchia of the subject.

14. The apparatus as claimed in claim 13, wherein the measured concentration of the specified gas includes nitric oxide.

15. An apparatus for monitoring the respiration of a subject, the apparatus comprising:
   a gas concentration sensor configured to measure a concentration of a specified gas in exhaled air by the subject; and
   a physical computer processor in communication with the sensor configured by machine-readable instructions to:

identify portions of the exhaled air that correspond to air exhaled from an upper airway, alveoli, and bronchia of a respiratory tract of the subject;
operate in a first mode to:
    activate the sensor, in response to identifying a portion of the exhaled air from the bronchia, to measure the concentration of the specified gas in only the exhaled air from the bronchia to facilitate monitoring asthma in the subject; and
    provide a first output indicating the concentration of the specified gas in the exhaled air from the bronchia of the subject; and
operate in a second mode to:
    activate the sensor, in response to identifying a portion of the exhaled air from the alveoli, to measure the concentration of the specified gas in only the exhaled air from the alveoli to facilitate monitoring pneumonia in the subject; and
    provide a second output indicating the concentration of the specified gas in the exhaled air from the alveoli of the subject.

16. The apparatus as claimed in claim 15, further comprising a user interface configured to receive user selection of the portions of exhaled air that corresponds to air exhaled from the upper airway, the alveoli, and the bronchia such that the processor is configured to identify and cause sampling of the exhaled air that corresponds to air exhaled from the upper airway, the alveoli, and/or the bronchia of the subject based on the user selection.

* * * * *